United States Patent
Im et al.

(10) Patent No.: US 10,161,013 B2
(45) Date of Patent: Dec. 25, 2018

(54) METHOD FOR THE ISOLATION AND PURIFICATION OF ANHYDROGALACTOSE

(71) Applicants: Dongjoong Im, Seoul (KR); Gyungsoo Kim, Yongin-si (KR)

(72) Inventors: Dongjoong Im, Seoul (KR); Gyungsoo Kim, Yongin-si (KR)

(73) Assignee: Biol Systems Co., Ltd., Jeollanam-Do (KR)

(*) Notice: Subject to any disclaimer, the term of this patent is extended or adjusted under 35 U.S.C. 154(b) by 30 days.

(21) Appl. No.: 15/004,256

(22) Filed: Jan. 22, 2016

(65) Prior Publication Data

US 2016/0208348 A1 Jul. 21, 2016

Related U.S. Application Data

(63) Continuation of application No. PCT/KR2011/003228, filed on Apr. 29, 2011.

(51) Int. Cl.
  *C13K 13/00* (2006.01)
  *C12P 19/02* (2006.01)

(52) U.S. Cl.
  CPC ............ *C13K 13/007* (2013.01); *C12P 19/02* (2013.01)

(58) Field of Classification Search
  None
  See application file for complete search history.

(56) References Cited

U.S. PATENT DOCUMENTS 6,518,302 B1    2/2003  Kobayashi
6,531,148 B1 *  3/2003  Enoki ................ A23L 3/3535
                                                        424/400

FOREIGN PATENT DOCUMENTS

KR    10-2009-0025221      3/2009
WO    WO200810568      *   9/2008

OTHER PUBLICATIONS

Tarafder et al. Journal of Chromatography A, 1195 (2008) 67-77.*
Tsuda. Isolation of Natural Products. Jan. 31, 2004.*
Lee et al. Acta Crystallogr Sect F Struct Biol Cryst Commun. Dec. 1, 2009;65(Pt 12):1299-301.*
Nathan et al. Appl Environ Microbiol. May 2006;72(5):3396-405.*
Int'l. Search Report of PCT/KR2011/003228 dated Jan. 11, 2012.
Heuer, C. et al.; "Chemical Engineering Science" (1995) vol. 50, No. 7, pp. 1115-1127.
Coq, B. et al., "Journal of Liquid Chromatography" (1981) vol. 4, pp. 237-249.
Ohta, Y. et al., Current Microbiology (2005) vol. 50, pp. 212-216.

* cited by examiner

*Primary Examiner* — Christian L Fronda
(74) *Attorney, Agent, or Firm* — Greer, Burns & Crain, Ltd.

(57) ABSTRACT

The present invention discloses a method for isolating and purifying anhydrogalactose. Using the method for isolating and purifying anhydrogalactose including the steps of preparing a sugar mixture containing anhydrogalactose produced through chemical synthesis and hydrolysis; and isolating anhydrogalactose by performing recycling preparative liquid chromatography (recycling-prep-LC) with the sugar mixture, highly pure anhydrogalactose can be efficiently isolated and purified in large amounts.

11 Claims, 5 Drawing Sheets

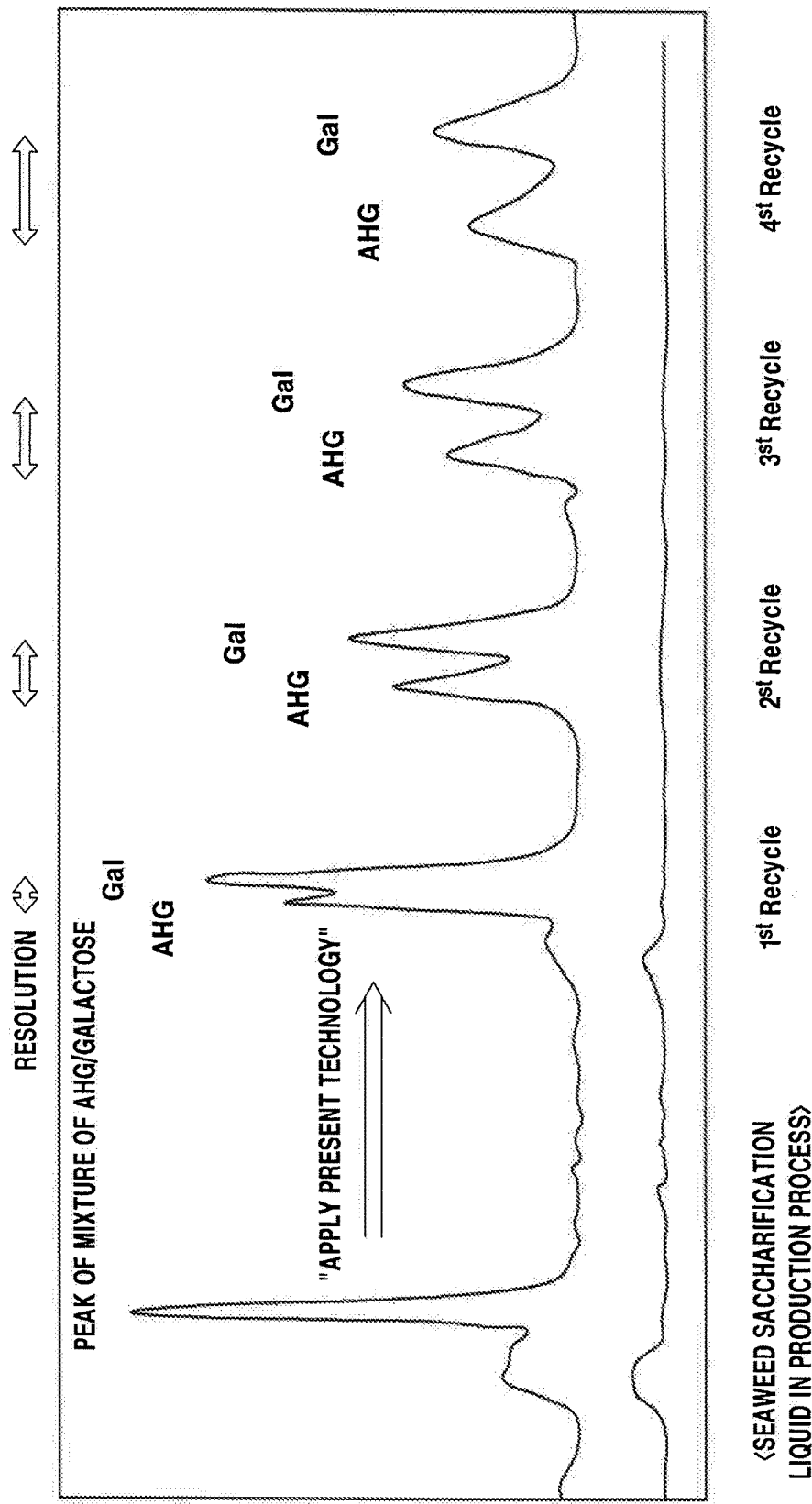

METHOD FOR THE ISOLATION AND PURIFICATION OF ANHYDROGALACTOSE

This is a continuation of International Application No. PCT/KR2011/003228, filed Apr. 29, 2011.

TECHNICAL FIELD

The invention relates to a method, for isolating and purifying anhydrogalactose, and more particularly, to a method for isolating anhydrogalactose from a sugar mixture produced through chemical synthesis or hydrolysis by using recycling preparative liquid chromatography (recycling-prep-LC).

BACKGROUND

Anhydrogalactose, particularly, 3,6-anhydro-L-galactose (3,6-AHG), 3,6-anhydro-D-galactose, etc. as one of sugars constituting seaweed are candidates of which functionality useful for development of a bioactive substance and applications to the pharmaceutical field is expected.

A lot of 3,6-AHG is mainly contained in seaweed and produced through saccharification using the seaweed as a source material 3,6-AHG produced through the saccharification is one of monosaccharides such as galactose and glucose which are products of the saccharification. Thus, 3,6-AHG is very similar to galactose and glucose in chemical structure and molecular weight. Therefore, it is difficult to isolate a large amount of 3,6-AHG with high purity by the conventional methods such as solvent extraction, adsorption, chromatography, and the like.

Currently, it is estimated that 3,6-AHG is globally produced and sold in small amounts, and it is sold at a very high price of about 300 dollars per 100 mg.

Up to now, anion-chromatography has been known as a method for isolation of 3,6-AHG, but it is suitable for micro-scale implementation only for analysis. Therefore, when applied to large-scale implementation, the anion-chromatography has problems of low durability of resin, high prices of source materials, and a decrease in isolation efficiency when isolation is performed for a long time and increased in amount.

Accordingly, a new method for mass production of anhydrogalactose, particularly 3,6-AHG at low cost is needed.

DETAILED DESCRIPTION OF THE INVENTION

Problems to be Solved by the Invention

The present inventors confirmed that it is possible to isolate pure anhydrogalactose from a mixture of similar monosaccharaides by performing a repetition cycle of recycling-prep-LC under specific conditions, and, thus, completed the present disclosure.

Therefore, one purpose of the present disclosure is to provide a method for isolating and purifying anhydrogalactose from a sugar mixture including anhydrogalactose produced through chemical synthesis or hydrolysis of a polysaccharide.

Further, another purpose of the present disclosure is to provide 3,6-anhydro-L-galactose isolated and purified by the above-described method for the isolation and purification.

However, problems to be solved by the present disclosure are not limited to the above-described problems. Although not described herein, other problems to be solved by the present disclosure can be clearly understood by those skilled in the art from the following descriptions.

Means for Solving the Problems

According to an aspect of the present disclosure, there is provided a method for isolating and purifying anhydrogalactose, comprising: preparing a sugar mixture containing anhydrogalactose produced through chemical synthesis or hydrolysis of a polysaccharide; and isolating anhydrogalactose by performing recycling-prep-LC with the sugar mixture.

In an embodiment, the anhydrogalactose may include 3,6-anhydro-L-galactose, but may not be limited thereto.

In another embodiment, the sugar mixture containing anhydrogalactose may be saccharification liquid obtained through saccharification of seaweed, but may not be limited thereto. In an embodiment, the process of obtaining saccharification liquid through the saccharification of seaweed may be performed by a method known in the art as disclosed in, for example, Korean Patent Laid-open Publication No. 10-2009-0025221. Korean Patent Laid-open Publication No. 10-2009-0025221 is incorporated herein by reference in its entirety.

In yet another embodiment, the seaweed may be seaweed containing anhydrogalactose or a polymer thereof, but may not be limited thereto.

In still another embodiment, the seaweed may be *Chondrus, Eucheuma, Gigartina, Pterocladia, Hypnea, Iridaea, Kappaphycus, Gellidium*, or *Gracilaria*, but may not be limited thereto.

In still another embodiment, the saccharification liquid may include 3,6-anhydro-L-galactose and galactose, but may not be limited thereto.

In still another embodiment, the step for isolating anhydrogalactose may include performing a repetition cycle of recycling-prep-LC one or more times with the sugar mixture to increase a difference in retention time between the anhydrogalactose and the other component in the sugar mixture, and fractionating and collecting anhydrogalactose only, but may not be limited thereto.

In still another embodiment, the recycling-prep-LC may be equipped with a column having a MWCO (Molecular Weight Cut-off) of from 100 to 2,000, but may not be limited thereto.

In still another embodiment, the recycling-prep-LC may be performed at a flow rate of from 0.1 ml/min to 20 ml/min, but may not be limited thereto.

In still another embodiment, the recycling-prep-LC may use an aqueous solvent, for example, water or alcohol as a mobile phase, but may not be limited thereto.

In another aspect of the present disclosure, there is provided anhydrogalactose isolated and purified by performing recycling-prep-LC from a sugar mixture containing anhydrogalactose produced through chemical synthesis or hydrolysis of a polysaccharide according to the above-described method of the present disclosure.

In an embodiment, there is provided anhydrogalactose obtained by being isolated and purified by performing recycling preparative liquid chromatography with a sugar mixture containing anhydrogalactose produced through chemical synthesis or hydrolysis of a polysaccharide.

In another embodiment, the anhydrogalactose may include 3,6-anhydro-L-galactose, but may not be limited thereto.

In yet another embodiment, the sugar mixture may be saccharification liquid containing a sugar compound obtained through saccharification of seaweed, but may not be limited thereto.

In still another embodiment, the saccharification liquid may include 3,6-anhydro-L-galactose and galactose, but may not be limited thereto.

In still another embodiment, the seaweed may be seaweed containing anhydrogalactose or a polymer thereof, but may not be limited thereto.

In still another embodiment, the seaweed may be *Chondrus, Eucheuma, Gigartina, Pterocladia, Hypnea, Iridaea, Kappaphycus, Gellidium,* or *Gracilaria,* but may not be limited thereto.

In yet another aspect of the present disclosure, there is provided a method for preparing anhydrogalactose from seaweed, comprising: producing saccharification liquid containing anhydrogalactose or a polymer thereof by treating raw seaweed or a polysaccharide substance extracted from seaweed with a lyase catalyst and/or a hydrolysis catalyst; and isolating anhydrogalactose by performing recycling preparative liquid chromatography with the saccharification liquid.

In an embodiment, the process of producing the saccharification liquid from seaweed may be performed by saccharification of seaweed known in the art as disclosed in, for example, Korean Patent Laid-open Publication No. 10-2009-0025221. Korean Patent Laid-open Publication No. 10-2009-0025221 is incorporated herein by reference in its entirety.

In another embodiment, the producing saccharification liquid may include reacting the raw seaweed at a temperature of from 60° C. to 300° C. using, a hydrolysis catalyst selected from the group consisting of sulfuric acid, HCl, HBr, $HNO_3$, $CH_3COOH$, HCOOH, $HClO_4$, $H_3PO_4$, PTSA, and commercial solid acid in a concentration of from about 0.05% to about 50%, but may not be limited thereto.

In yet another embodiment, the saccharification liquid may include 3,6-anhydro-L-galactose and galactose, but may not be limited thereto.

All the descriptions relating to the method for isolating, and purifying anhydrogalactose in accordance with the present disclosure may be applied to the method for preparing anhydrogalactose from seaweed in accordance with the present disclosure, and redundant descriptions will be omitted for convenience.

Effect of the Invention

According to the present disclosure, it is possible to isolate and purify highly pure anhydrogalactose from hydrolysate containing a precursor, a sugar mixture of similar monosaccharaides, and anhydrogalactose by performing a repetition cycle of recycling-prep-LC. By scaling up recycling-prep-LC, it is possible to manufacture a system for the isolation and purification of anhydrogalactose in large amounts, and also possible to produce anhydrogalactose in large amounts at low cost. Further, it is possible to easily isolate and purify anhydrogalactose from saccharification liquid obtained through saccharification of seaweed by the above-described method for the isolation and purification according to the present disclosure. Thus, according to the present disclosure, it is possible to isolate and purify highly pure 3,6-anhydro-L-galactose which is expected to usefully function as a bioactive substance and medicine.

BRIEF DESCRIPTION OF THE DRAWINGS

FIG. 5 is a graph showing a result of isolation of 3,6-AHG from seaweed saccharification liquid by, performing recycling preparative liquid chromatography in accordance with an example of the present disclosure.

BEST MODE FOR CARRYING OUT THE INVENTION

Figure 1:
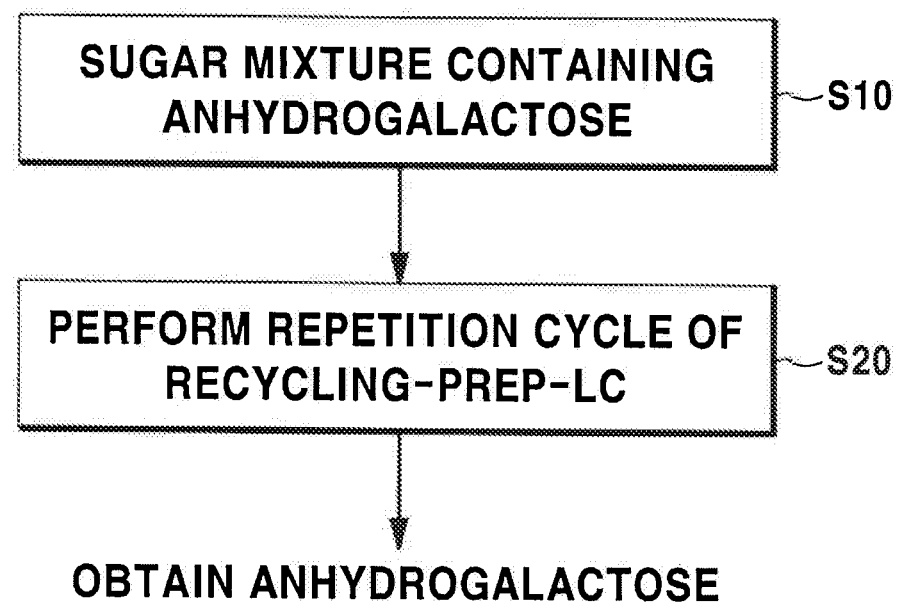
FIG. 1 is a flowchart of a process for isolation of 3,6-AHG in accordance with an example of the present disclosure.

Hereinafter, embodiment and examples of the present disclosure will be described in detail with reference to the accompanying drawings so that the present disclosure may be readily implemented by those skilled in the art. However, it is to be noted that the present disclosure is not limited to the embodiments and examples but can be embodied in various other ways. In drawings, parts irrelevant to the description are omitted for the simplicity of explanation, and like reference numerals denote like parts through the whole document of the present disclosure.

The terms used herein are used only to describe specific examples, but do not intend to limit the present disclosure. A singular expression includes a plural expression unless it is clearly construed in a different way in the context. The terms used herein, such as "including" or "having", are used only to designate the features, numbers, steps, operations, constituent elements, parts, or combinations thereof described in the specification, but should be construed not to exclude existence or addition of one or more other features, numbers, steps, operations, constituent elements, parts, or combinations thereof.

Through the whole document of the present disclosure, the term "on" that is used to designate a position of one layer or element with respect to another layer or element includes both a case that the one layer or element is adjacent to the another layer or element and a case that any other layer or element exists between these two layers or elements.

Through the whole document of the present disclosure, the term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party. Through the whole document of the present disclosure, the term "step of" does not mean "step for".

Hereinafter, a method for isolating and purifying anhydrogalactose in accordance with an embodiment of the present disclosure will be described in detail.

According to an embodiment of the present disclosure, there is provided a method for isolating and purifying anhydrogalactose, including: preparing a sugar mixture containing anhydrogalactose produced through chemical synthesis or hydrolysis of a polysaccharide (S10); and isolating anhydrogalactose by performing recycling preparative liquid chromatography (recycling-prep-LC) with the sugar mixture (S20).

The step of preparing the sugar mixture (S10) may be performed through various chemical synthesis or hydrolysis processes in which anhydrogalactos can be produced, and for example, a sugar mixture containing anhydrogalactose may be obtained through saccharification of biomass. Herein, various saccharification processes known in the art may be employed for saccharification of the biomass. For example, any method of producing a saccharification liquid through saccharification of seaweed may be employed without particular limitation.

For example, the anhydrogalactose is 3,6-anhydro-L-galactose produced through saccharification of seaweed. However, other anhydrogalactose such as 3,6-anhydro-D-galactose which can be produced through chemical synthesis is not excluded, and the method can be applied to various isomers, derivatives and analogues of, galactose. It is possible to isolate and purify various anhydroglucose, for example, 1,6-anhydro-D-glucose by the same method.

If a saccharification liquid is produced through saccharification of seaweed, the seaweed is not particularly limited, but desirably, it may be seaweed containing anhydrogalactose or a polymer thereof as components. For example, the seaweed may include *Chondrus, Eucheuma, Gigartina, Pterocladia, Hypnea, Iridaea, Kappaphycus, Gellidium,* or *Gracilaria*. In particular, red, algae such as agar may be used. The saccharification liquid produced through saccharification of the seaweed may include 3,6-AHG and galactose.

After the sugar mixture is prepared, anhydrogalactose is isolated from the sugar mixture by performing recycling-prep-LC to the sugar mixture (S20).

The recycling-prep-LC is a kind of liquid chromatography, and refers to liquid chromatography of recycling a sample passing through a column without being isolated and injecting the sample into the column regardless of the number of times.

Liquid chromatography is a general term referring to chromatography using a liquid as a mobile phase. The liquid chromatography is broadly classified into liquid-solid chromatography and liquid-liquid chromatography (also referred to as liquid partition chromatography). The liquid chromatography includes droplet counter-current chromatography, emulsion chromatography, and field-flow fractionation in a broad sense. The liquid chromatography may include planar chromatography classified into column chromatography, thin-layer chromatography, and paper chromatography according to the form of a stationary phase. The liquid chromatography includes high-performance liquid chromatography (HPLC) using high-performance mechanized column chromatography in a narrow sense. The HPLC is widely used these days as the most representative liquid chromatography. Liquid chromatography has a wide scopes of samples as compared with gaseous chromatography and has very little problem with thermal stability and volatility. All of low molecular, high molecular, polar, non-polar samples can be used as an analysis target. Further, in the liquid chromatography, various mobile phases may be selected and various kinds of interactions may be used for isolation. Therefore, liquid chromatography has been applied to the field which cannot be analyzed by gaseous chromatography or the field which cannot be satisfied with resolution and quantitative property of planar chromatography and accomplished a great deal of achievements. Furthermore, liquid chromatography has the advantage of easy fractionation and collection that is the original purpose of chromatography.

The recycling-prep-LC is a method of inducing a sample into a column inlet while the sample is isolated and eluted passing through a column according to a conventional method, and then isolating, the sample again. Theoretically, it is possible to increase the number of times of recycling to infinity. Herein, the resolution of the sample is increased, and, thus, it can be applied to a sample to be very difficult to isolate. However, since the sample is diluted in a solvent as the resolution is increased, conditions for optimizing the resolution for each sample are needed. The conditions to optimally isolate an unknown sample include a kind of column, a speed of an eluate, an amount of an injected sample, the number of times of recycling. When the optimized results of these values are produced, it is possible to isolate/fractionate and collect a desired sample.

According to an embodiment of the present disclosure, in the recycling-prep-LC, by performing a repetition cycle of liquid chromatography one or more times with the sugar mixture to increase a difference in retention time between the anhydrogalactose and the other component in the sugar mixture, it is possible to fractionate and collect anhydrogalactose only. Desirably, the repetition cycle may be performed two or more times, three or more times, four or more times, or five or more times. More desirably, the repetition cycle may be performed four or more times. If it is possible to fractionate and collect anhydrogalactose only since a difference in retention time between the anhydrogalactose and the other components is increased by repeating the cycle, the upper limit of the number of times of performing the repetition cycle is not particularly limited. If a difference in retention time between the anhydrogalactose and the other component is increased to 5 minutes to 10 minutes, it is possible to very easily fractionate and collect anhydrogalactose only.

A column used in, the recycling-prep-LC may be a column having a MWCO (Molecular Weight Cut-off) of from about 100 to about 5,000, desirably a column having a MWCO of from about 100 to about 2,000, and most desirably a column having a MWCO of about 2,000 in order to isolate anhydrogalactose, particularly 3,6-anhydro-L-galactose.

A flow rate at which the recycling-prep-LC is performed may be from about 0.1 ml/min to about 100 ml/min, desirably from about 0.1 ml/min to about 20 ml/min. For example, if 3,6-AHG is isolated, the recycling-prep-LC may be performed at a flow rate of about 3.5 ml/min, and a flow rate may be suitably set for a large-scale system.

As a mobile phase of the recycling-prep-LC, an aqueous solvent such as water, alcohol, and the like may be used. Desirably, water may be used as a mobile phase.

By the above-described method for isolating and purifying the present disclosure, it is possible to selectively isolate specific anhydrogalactose wanted to be isolated from a mixture of various monosaccharaides similar in chemical structure and molecular weight and produced through saccharification or chemical synthesis of a polysaccharide such as seaweed. Further, by deducing isolation conditions suitable for each kind of anhydrogalactose, it is possible to isolate and purify highly pure anhydrogalactose in large amounts. In an embodiment of the present disclosure, it is possible to isolate and purify anhydrogalactose with a high purity of, but not limited to, 99% or more or 99.9% or more.

Hereinafter, preferred examples will be described for understanding of the present disclosure. However, the following examples are provided only for more easily understanding of the present disclosure, but the present disclosure is not limited thereto.

Example 1

Isolation of 3,6-AHG from Mixed Solution Containing 3,6-AHG and Galactose

Figure 2:
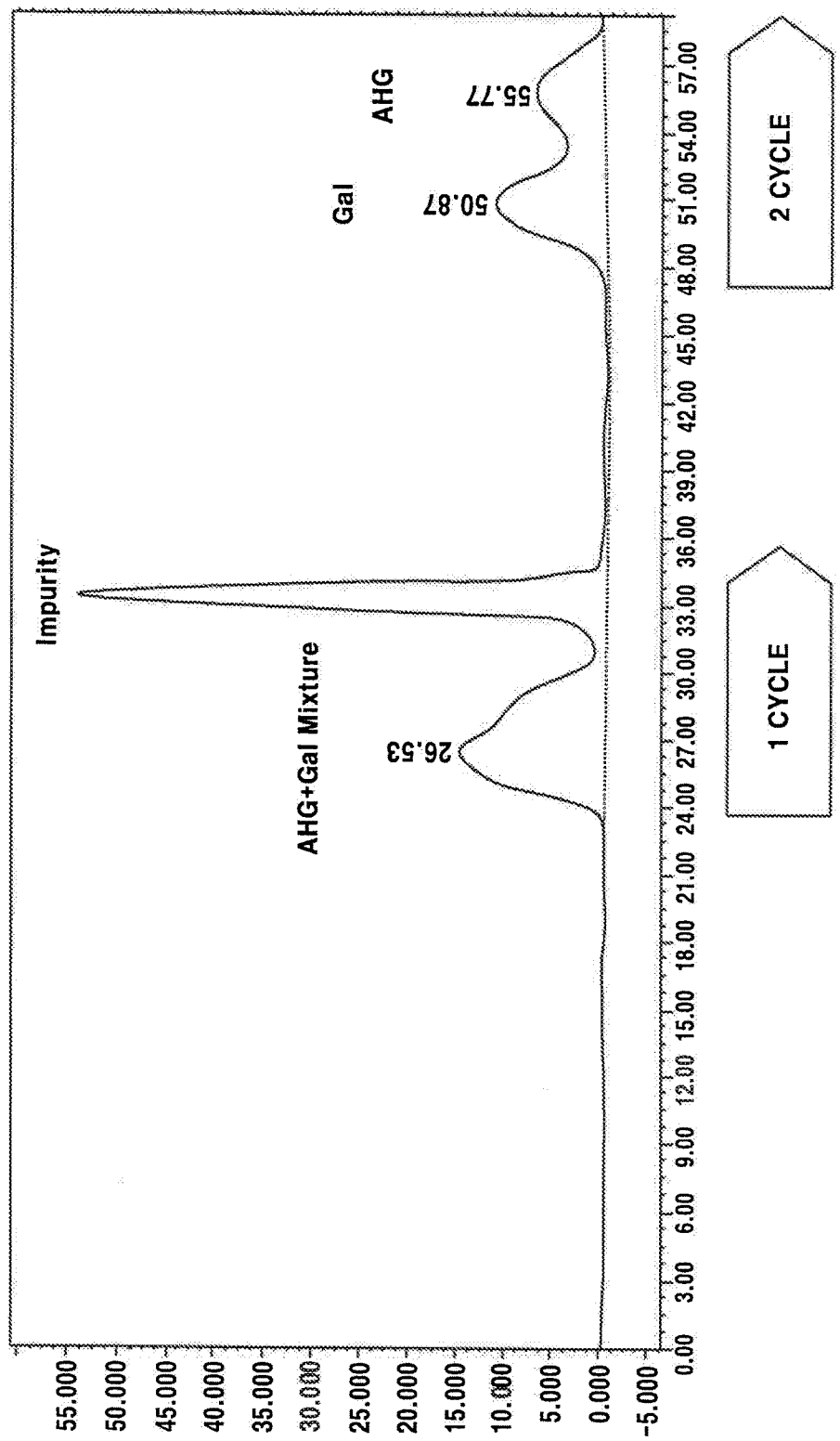
FIG. 2 is a graph showing a result of isolation of 3,6-AHG by performing a cycle of recycling preparative liquid chromatography once and twice in accordance with an example of the present disclosure.
Figure 3:
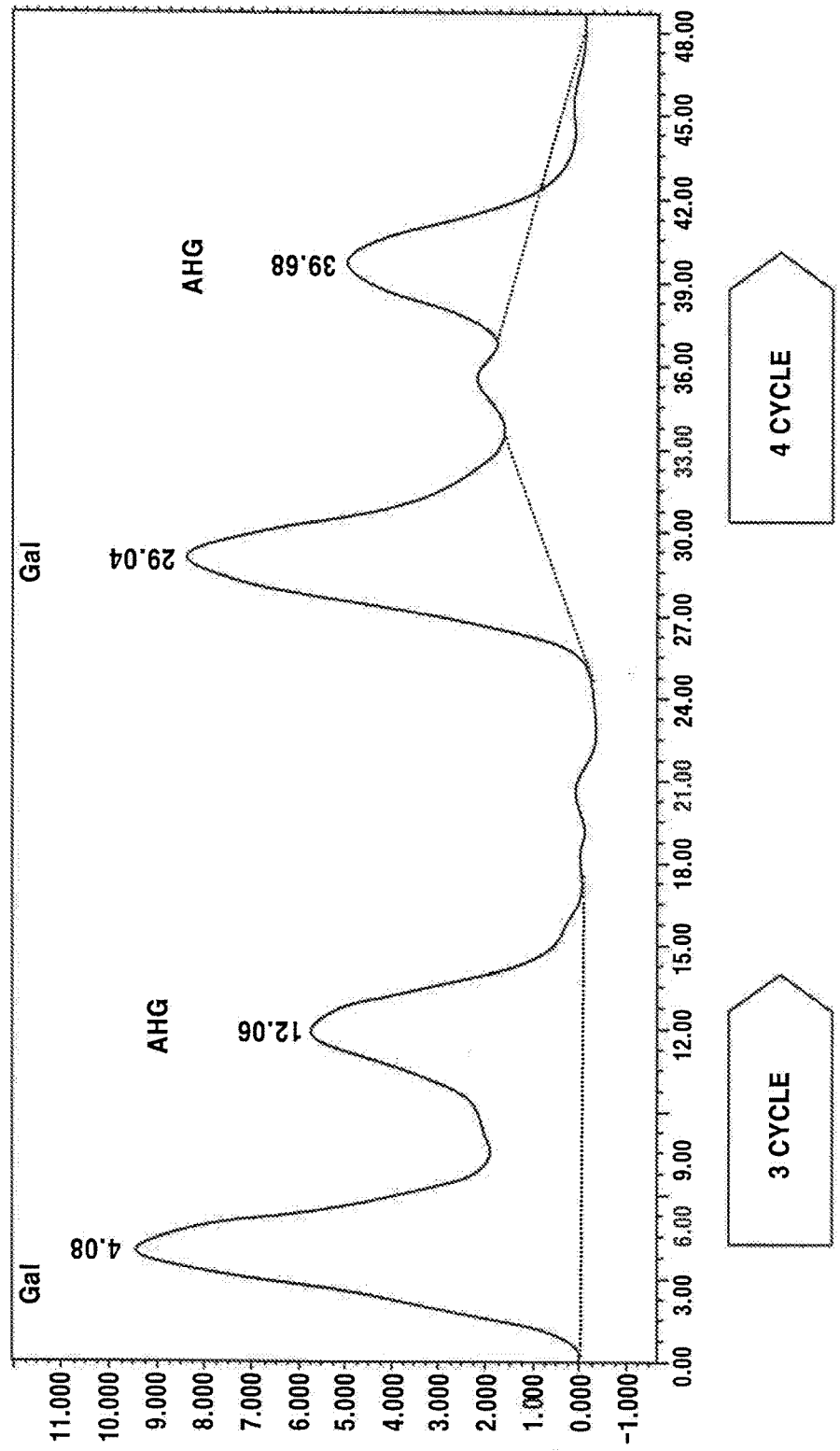
FIG. 3 is a graph showing a result of isolation of 3,6-AHG by performing a cycle of recycling preparative liquid chromatography three times and four times in accordance with an example of the present disclosure.

A 500 ppm (DW) mixed solution containing 3,6-AHG and galactose was prepared, and isolation was attempted using recycling-prep-LC under the conditions as follows:

A LC-9101 recycling-prep-LC device equipped with a W251 (MWCO 2,000) column (manufactured by JAI)
Flow rate: 3.5 ml/min
Injection Vol.: 8 ml (500 ppm)
Mobile phase: water (18 M)
Refractive Index: Oven, sensitivity 15
Chart speed: 150 mm/h Recycling-prep-LC was performed under the above-described conditions, and an isolation result from a cycle performed once and twice was as displayed in FIG. 2 and an isolation result from a cycle performed three times and four times was as displayed in FIG. 3.

When the cycle was performed once, it was difficult to isolate two substances, i.e., 3,6-AHG and galactose, isolated from other impurities under the above-described isolation conditions due to an overlap of the two substances. When the cycle was performed twice and three times, a difference in retention time between the two substances was increased to 5 minutes to 8 minutes, and, thus, the two substances could be isolated by recycling-prep-LC. Further, a remarkable increase in resolution was observed. When the cycle was performed four times, 3,6-AHG and galactose were completely isolated, and then separately fractionated and collect them. Thus, 3,6-AHG having a purity of 99% or more was obtained [Table 1: see the retention time between components in a sample].

Figure 4:
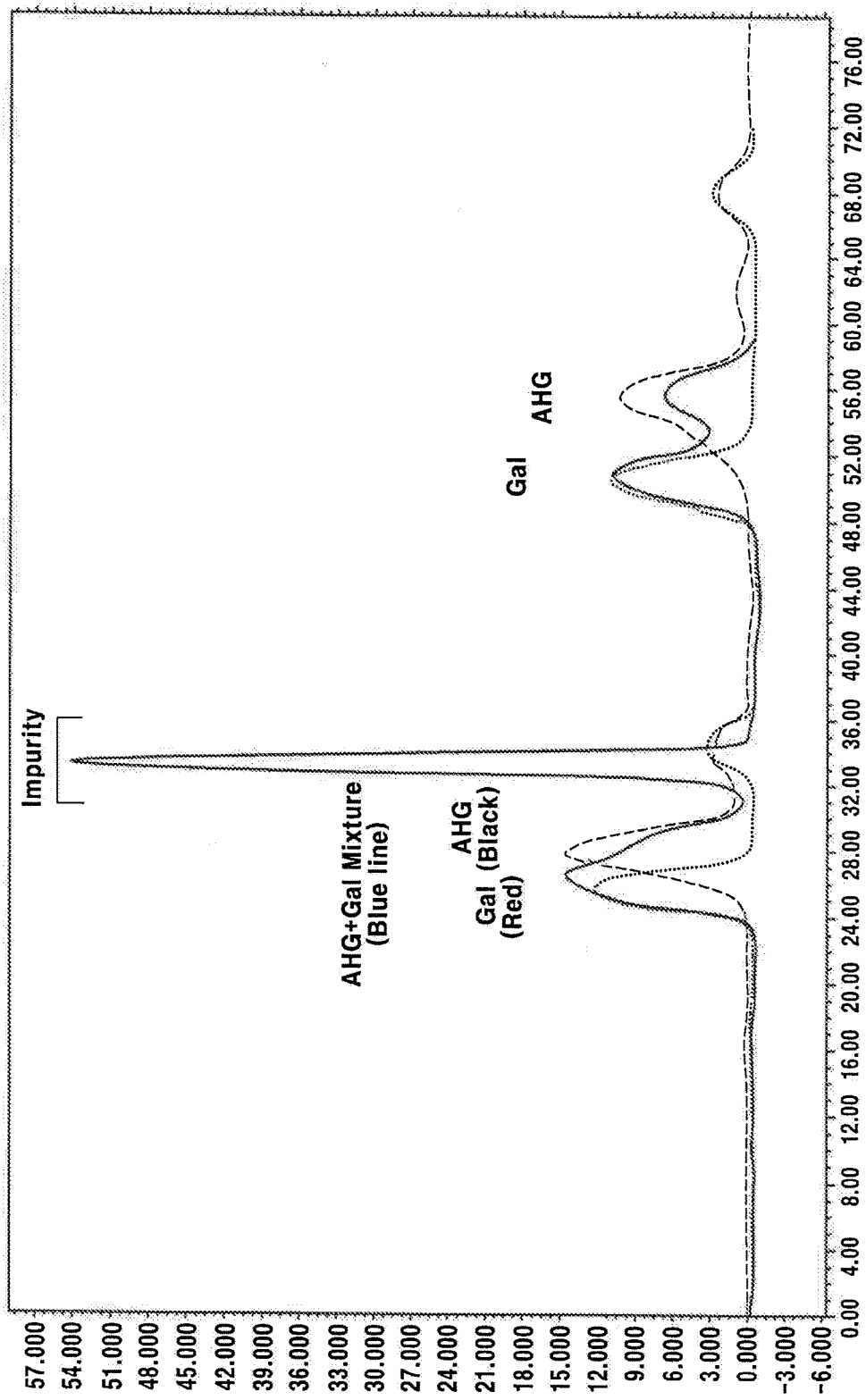
FIG. 4 is a graph showing a result of isolation of 3,6-AHG by performing recycling preparative liquid chromatography in accordance with an example of the present disclosure.

A result of comparison between the graphs for identification of each substance of 3,6-AHG and galactose as a result of the cycle performed twice and three times after the cycle performed once was as shown in FIG. 4. It was observed that as the number of times of performing the cycle increased, a difference in retention time between galactose and 3,6-AHG increased. The above-described result was summarized as shown in Table 1.

TABLE 1

| Number of Cycle | Time Interval between Peaks (min) | Retention Time (min) Galactose | Retention Time (min) 3,6-AHG |
|---|---|---|---|
| 1 | — | 26.53 | *ND |
| 2 | 4.9 | 50.87 | 55.77 |
| 3 | 7.98 | 4.08 | 12.06 |
| 4 | 10.64 | 29.04 | 39.68 |

*ND: No difference

Example 2

Anhydrogalactose was isolated and purified in the same manner as Example 1 except that saccharification liquid containing a sugar compound obtained through saccharification of seaweed was used as a sugar mixture instead of the mixed solution containing 3,6-AHG and galactose. *Gracilaria* was used as the seaweed.

To be specific, *Gracilaria* as a kind of red algae was dried and crushed to be used as a substrate, and 75 g of the substrate was mixed with 150 ml of 1% sulfuric acid aqueous solution and then put into a 4 L-conical flask and reacted at 121° C. for 15 minutes. Then, the temperature was lowered to room temperature to obtain a saccharification liquid. The obtained saccharification liquid was neutralized with $CaCO_3$ and centrifuged at 8,000 rpm for 10 minutes using a centrifuge (VS-150FN, Vision Science Co., LTD., Korea) to remove $CaSO_4$. Then, the sulfuric acid aqueous solution (0.5% to 4.0%) containing the substrate was put into an autoclave reactor according to a S/L ratio (5.5% to 15.0%), and saccharification was conducted at a preset temperature range (from about 80° C. to about 200° C.) for 4 hours. Thus, saccharification liquid containing 3,6-AHG and galactose was obtained. The process of obtaining saccharification liquid was performed with reference to the disclosure of Korean Patent Laid-open Publication No. 10-2009-0025221.

Then, an isolation and purification result from a cycle of recycling-prep-LC performed once to four times under the same conditions as Example 1 using the obtained saccharification liquid was as displayed in FIG. 5.

Similar to Example 1, when the cycle was performed once, it was difficult to isolate 3,6-AHG and galactose due to an overlap of the two substances, and when the cycle was performed twice and three times, a difference in retention time between the two substances was increased, and, thus, the two substances could be isolated by recycling-prep-LC. Further, when the cycle was performed four times, 3,6-AHG and galactose were completely isolated, and then separately fractionated and collect them. Thus, 3,6-AHG having a high purity (99% or more) was obtained.

While this invention has been described with reference to preferred examples of the present disclosure, it is to be understood by those skilled in the art that the present disclosure can be modified and changed in various ways within the spirit and scope of the appended claims.

We claim:

1. A method for isolating and purifying 3,6-anhydro-L-galactose, comprising:
   preparing a sugar mixture containing 3,6-anhydro-L-galactose and at least one other sugar, wherein the sugar mixture is produced through chemical synthesis or hydrolysis of a polysaccharide; and
   isolating 3,6-anhydro-L-galactose from the at least one other sugar by performing recycling preparative liquid chromatography with the sugar mixture, wherein the isolating 3,6-anhydro-L-galactose includes performing a repetition cycle of recycling preparative liquid chromatography four times with the sugar mixture to increase a difference in retention time between the 3,6-anhydro-L-galactose and the at least one other sugar in the sugar mixture,
   and fractionating and collecting 3,6-anhydro-L-galactose having a purity of at least 99%,
   wherein the recycling preparative liquid chromatography uses a column having a MWCO (Molecular Weight Cut-off) of from 100 to 2,000 and is performed at a flow rate of from 0.1 ml/min to 30 ml/min.

2. The method for isolating and purifying 3,6-anhydro-L-galactose of claim 1, wherein the sugar mixture is saccharification liquid obtained through saccharification of seaweed.

3. The method for isolating and purifying 3,6-anhydro-L-galactose of claim 2, wherein the seaweed includes anhydrogalactose or a polymer thereof.

4. The method for isolating and purifying 3,6-anhydro-L-galactose of claim 2, wherein the seaweed includes *Chondrus, Eucheuma, Gigartina, Pterocladia, Hypnea, Iridaea, Kappaphycus, Gellidium*, or *Gracilaria*.

5. The method for isolating and purifying 3,6-anhydro-L-galactose of claim 2, wherein the saccharification liquid includes 3,6-anhydro-L-galactose and galactose.

6. The method for isolating and purifying 3,6-anhydro-L-galactose of claim 1, wherein only 3,6-anhydro-L-galactose is fractionated and collected.

7. The method for isolating and purifying 3,6-anhydro-L-galactose of claim 1, wherein the recycling preparative liquid chromatography uses water or alcohol solvent as a mobile phase.

8. A method for preparing 3,6-anhydro-L-galactose from seaweed, comprising:
producing saccharification liquid containing 3,6-anhydro-L-galactose and at least one other sugar by treating raw seaweed or a polysaccharide substance extracted from seaweed with a lyase and/or a hydrolysis catalyst;
isolating 3,6-anhydro-L-galactose from the at least one other sugar by performing repetition cycle of recycling preparative liquid chromatography four times with the saccharification liquid to increase a difference in retention time between the 3,6-anhydro-L-galactose and the at least one other sugar in the saccharification liquid, and
collecting 3,6-anhydro-L-galactose having a purity of at least 99%,
wherein the recycling preparative liquid chromatography uses a column having a MWCO (Molecular Weight Cut-off) of from 100 to 2,000 and is performed at a flow rate of from 0.1 ml/min to 20 ml/min.

9. The method for preparing 3,6-anhydro-L-galactose from seaweed of claim 8, wherein the producing the saccharification liquid includes reacting the raw seaweed at a temperature of from 60° C. to 300° C. using a hydrolysis catalyst selected from a group consisting of sulfuric acid, HCl, HBr, $HNO_3$, $CH_3COOH$, HCOOH, $HClO_4$, $H_3PO_4$, PTSA, and commercial solid acid in a concentration of from about 0.05% to about 50%.

10. The method for isolating and purifying 3,6-anhydro-L-galactose of claim 1, wherein the sugar mixture is produced through hydrolysis of a polysaccharide by reacting a raw seaweed at a temperature of from 60° C. to 300° C. using a hydrolysis catalyst selected from a group consisting of sulfuric acid, HCl, HBr, $HNO_3$, $CH_3COOH$, HCOOH, $HClO_4$, $H_3PO_4$, PTSA, and commercial solid acid in a concentration of from about 0.05% to about 50%.

11. The method for isolating and purifying 3,6-anhydro-L-galactose of claim 10, wherein the seaweed includes *Chondrus, Eucheuma, Gigartina, Pterocladia, Hypnea, Iridaea, Kappaphycus, Gellidium,* or *Gracilaria*.

* * * * *